United States Patent [19]

Zinnes et al.

[11] 4,074,048
[45] * Feb. 14, 1978

[54] PROCESS FOR THE PREPARATION OF 4-HYDROXY-2H-1,2-BENZOTHIAZINE-3-CARBOXAMIDE 1,1-DIOXIDES

[75] Inventors: Harold Zinnes, Rockaway; Neil A. Lindo, New Providence; John Shavel, Jr., Mendham, all of N.J.

[73] Assignee: Warner-Lambert Company, Morris Plains, N.J.

[*] Notice: The portion of the term of this patent subsequent to May 18, 1993, has been disclaimed.

[21] Appl. No.: 685,011

[22] Filed: May 10, 1976

[51] Int. Cl.² ............... C07D 279/02; C07D 417/12
[52] U.S. Cl. .......................... 544/49; 260/304 R; 260/294.8 D; 424/246
[58] Field of Search .................. 260/243 R; 544/49

[56] References Cited

U.S. PATENT DOCUMENTS

| 3,284,450 | 11/1966 | Kraaijeveld et al. | 260/243 |
| 3,492,296 | 1/1970 | Zinnes et al. | 260/243 |
| 3,501,466 | 3/1970 | Rasmussen | 260/243 |
| 3,957,772 | 5/1976 | Fabian et al. | 260/243 |

Primary Examiner—John M. Ford
Attorney, Agent, or Firm—Albert H. Graddis; Frank S. Chow; Anne M. Kelly

[57] ABSTRACT

A novel process for preparing 4-hydroxy-2H-1,2-benzothiazine-3-carboxamide 1,1-dioxides is disclosed. The process involves the base catalyzed rearrangement of a saccharinacetamide of structure I to give II,

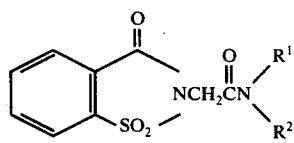

I

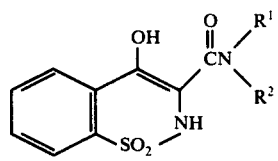

II wherein $R^1$ is hydrogen or lower alkyl and $R^2$ is lower alkyl, aryl or a heterocyclic ring selected from the group consisting of pyridyl, substituted-pyridyl, and thiazolyl. Compounds of the formula II have useful anti-inflammatory properties. In addition, they can be used as intermediate in the preparation of known anti-inflammatory agents.

1 Claim, No Drawings

PROCESS FOR THE PREPARATION OF 4-HYDROXY-2H-1,2-BENZOTHIAZINE-3-CARBOXAMIDE 1,1-DIOXIDES

BACKGROUND OF THE INVENTION

1. Field of the Invention

The present invention is concerned with a new process for preparing 4-hydroxy-2H-1,2-benzothiazine-3-carboxamide 1,1-dioxides, starting with amide-substituted-2,3-dihydro-3-oxo-1,2-benzisothiazole-2-acetamide 1,1-dioxides.

2. Description of the Prior Art

The preparation of certain 4-hydroxy-2H-1,2-benzothiazine-3-carboxamides by the rearrangement of specific saccharin derivatives is known. For example, Lombardino, in U.S. Pat. No. 3,591,584, and in J. Med. Chem. 14:1171–1175 (1971), discloses the use of saccharin acetic acid esters (3-oxo-1,2-benzisothiazoline-2-acetic acid methyl ester) to prepare 3,4-dihydro-4-oxo-1,2-benzothiazine-3-carboxylate 1,1-dioxide esters which are then alkylated on the 2-position and further treated with an amine to obtain the corresponding carboxamides. The use of a similar method to prepare 4-hydroxy-2H-1,2-benzothiazine-3-carboxamide 1,1-dioxide is described by Rasmussen in U.S. Pat. No. 3,501,466.

Zinnes, et al., describe a similar reaction starting with the analogous methyl ketone, in J. Org. Chem. 30:2241–2246 (1975).

Fabian, et al., in U.S. Ser. No. 577,567, now U.S. Pat. No. 3,987,038, filed May 21, 1975, and in U.S. Ser. No. 577,568, filed May 21, 1975, now U.S. Pat. No. 3,957,772, disclose the rearrangement of 2,3-dihydro-N-(5-methyl-3-isoxazolyl)-3-oxo-1,2-benzisothiazole-2-acetamide 1,1-dioxide to 1-{[5-(4-hydroxy-2H-1,2-benzothiazin-3-yl)-1,2,4-oxadiazol-3-yl]methyl} ethanone S,S-dioxide which upon methylation and further treatment, undergoes a second rearrangement to form 4-hydroxy-3-(5-methyl-3-isoxazolylcarbamoyl)-2-methyl-2H-1,2-benzothiazine 1,1-dioxide.

DESCRIPTION OF THE PARTICULAR EMBODIMENTS

According to this invention it has been found that 4-hydroxy-2H-1,2-benzothiazine-3-carboxamide 1,1-dioxides can be prepared by direct rearrangement of a corresponding substituted saccharinacetamide. Thus, a compound of the formula I:

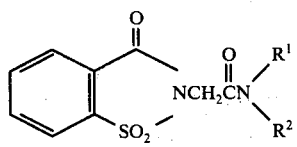

wherein $R^1$ is hydrogen or lower alkyl and $R^2$ is lower alkyl, aryl or a heterocyclic ring selected from the group consisting of pyridyl, substituted-pyridyl, and thiazolyl, is reacted with an alkali or alkaline earth metal alkoxide of a lower alcohol in an inert solvent, followed by acidification, to obtain a compound of the formula II:

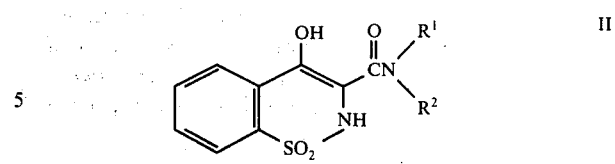

wherein $R^1$ and $R^2$ are as described above in formula I. Typically, rearrangement of compound I is effected using sodium methoxide in an inert solvent such as dimethylformamide or dimethylsulfoxide at temperatures ranging from about 35° C. to about 90° C.; for acidification, a mineral acid, for example HCl, or an organic acid such as acetic acid is used.

In the preferred process of the invention, there is used as the starting material, a compound of the formula I wherein $R^1$ is hydrogen or 1 to 4 carbon lower alkyl; $R^2$ is 1 to 4 carbon lower alkyl; phenyl; mono- or di-substituted phenyl wherein the substituent is 1 to 4 carbon lower alkyl or lower alkoxy, halogen or trifluoromethyl and the like; 2-pyridyl, or 2-substituted pyridyl wherein the substituent is 1 to 4 carbon lower alkyl or halogen. In a most preferred embodiment of the invention, there is used as the starting material a compound having the formula I wherein $R^1$ is hydrogen or methyl and $R^2$ is phenyl or 2-pyridyl. Correspondingly substituted 4-hydroxy-2H-1,2-benzothiazine-3-carboxamide 1,1-dioxides are obtained using the aforementioned preferred starting materials.

Starting materials having the formula I are generally prepared from sodium saccharin according to known chemical procedures, or obvious variations thereof. For example, sodium saccharin is reacted with an appropriately substituted α-haloacetamide to obtain a correspondingly substituted saccharin acetamide. Starting materials having the formula I are best prepared by first forming saccharin acetic acid (also known as 2-carboxymethyl saccharin, compound III), which is then reacted with a suitable amine to form the desired saccharin starting material. In this manner, compound III may be reacted with 2-aminopyridine in an inert solvent in the presence of a water scavenger such as dicyclohexyl carbodiimide to form starting material I where $R^1$ is hydrogen and $R^2$ is 2-pyridyl (also known as 2-[(N-2-pyridyl carbamoyl)methyl] saccharin, compound IV). An alternate method for obtaining aforementioned 2-[(N-2-pyridyl carbamoyl)methyl] saccharin, compound IV, involves the reaction of compound III with 2-aminopyridine in an inert solvent in the presence of N-ethoxy carbonyl-2-ethoxy-1,2-dihydroquinoline (EEDQ). Other starting materials having the formula I may be prepared by variations of the above mentioned procedures.

Compounds of the invention having the formula II have antiinflammatory activity but may also be used as intermediates in the preparation of other known anti-inflammatory agents. Thus, compounds of the formula II may be alkylated on the ring nitrogen to give known anti-inflammatory agents such as 4-hydroxy-2-methyl-N-(2-pyridyl)-2H-1,2-benzothiazine-3-carboxamide 1,1-dioxide. The alkylation is conducted according to conventional procedures using standard alkylating reagents, such as methyl iodide or dimethyl sulfate in an inert solvent in the presence of a base. Typically, a methylation reaction may be conducted using methyl iodide in dimethylformamide in the presence of sodium hydride.

The final compounds II prepared according to the process of this invention have useful anti-inflammatory properties. When administered orally to rats at a dose of 50-200 mg/kg, they are able to cause reduction in swelling of the paw induced by injection into the foot pads of an irritant such as carrageenin.

Generally speaking, compounds of the invention having formula II are indicated in conditions such as pain resulting from arthritis, bursitis, and the like. A daily dosage regimen of about 1.0 grams to about 2 grams in several divided doses is recommended for a mammal weight of about 70 kg body weight to relieve the pain and swelling associated with these conditions. Compounds having the formula II may be administered either orally or by injection.

In order to use compounds having the formula II, they are formulated into dosage forms such as tablets or syrups by blending with an inert pharmaceutical carrier such as lactose or simple syrup by methods well known to the pharmacists art. For injectionable dosage forms, the compounds prepared according to this invention are formulated with vehicles such as water, peanut oil, sesame oil, and the like. In these dosage forms, the active ingredient is from about 0.5 grams to 1 gram per dosage unit.

The following definitions apply to all of the compounds and reaction procedures of this invention, as well as to reagents and intermediates used in the preparation thereof: alkyl is meant to include 1 to 7 carbon alkyl, preferably 1 to 4 carbon alkyl (this definition also applies to the alkyl portion of alkoxy); halogen is meant to include chlorine, bromine and iodine; the term alkali and alkaline earth metal is meant to include sodium, potassium, calcium and the like; the term lower alcohol is meant to include 1 to 5 carbon, straight or branched chain alcohols; the term base is meant to include those bases commonly used in reaction media, such as sodium hydroxide, potassium hydroxide, pyridine, triethylamine, sodium hydride, potassium hydride, calcium hydride, and the like.

In order to further illustrate this invention, the following examples are provided:

EXAMPLE 1

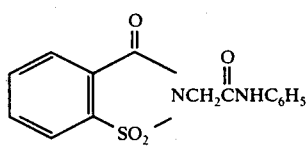

2-[(N-Phenylcarbamoyl)methyl]saccharin.

A solution of 22.6g (0.11 mole) of sodium saccharin and 16.7g (0.1 mole) of N-chloroacetylaniline in 150ml of dimethylformamide is heated on a steam bath for one hour, allowed to stir at room temperature for 16 hrs. and poured into icewater. The resulting precipitate is collected and dissolved in dichloromethane. This solution is dried over magnesium sulfate, and the solvent is evaporated. The residue is recrystallized from methanol to give 19.9g of product, mp. 180°-182° C.

EXAMPLE 2

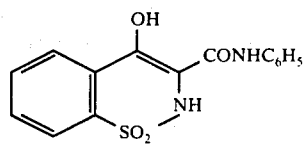

4-Hydroxy-N-phenyl-2H-1,2-benzothiazine-3-carboxamide 1,1-dioxides

A solution of 9.5g (0.03 mole) of 2-[(N-phenylcarbamoyl)methyl] saccharin in 50ml of dimethylformamide is heated to 50° C and 5.4g (0.1 mole) of sodium methoxide is added all at once with efficient stirring, whereupon the temperature rises to 75° C. The dark mixture is heated on a steam bath for 10 minutes, allowed to cool to room temperature and poured into ice-water containing excess hydrochloric acid. The resulting precipitate is collected and recrystallized from methanol to give 2.3g of product, mp. 270° C dec. It is shown to be identical with an authentic sample prepared by reaction of aniline with ethyl 4-hydroxy-2H-1,2-benzothiazine-3-carboxylate 1,1-dioxide as described by Zinnes et al., *J. Med. Chem.*, 16: 44 (1973).

EXAMPLE 3

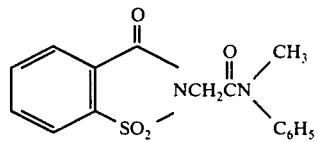

2-[(N-Methyl-N-phenylcarbamoyl)methyl]saccharin

A solution of 22.6g (0.11 mole) of sodium saccharin and 18.1g (0.1 mole) of N-chloroacetyl-N-methylaniline in 150ml of dimethylformamide is heated on a steam bath for 4 hrs., allowed to stir at room temperature for 16 hrs. and poured into ice-water. The resulting precipitate is collected and dissolved in dichloromethane. This solution is dried over magnesium sulfate, and the solvent is evaporated. Recrystallization from methanol gave 21g of product, mp. 205°-206° C.

EXAMPLE 4

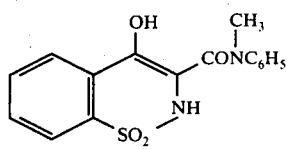

4-Hydroxy-N-methyl-N-phenyl-2H-1,2-benzothiazine-3-carboxamide 1,1-dioxide

To a solution of 9.9g (0.03 mole) of 2-[(N-methyl-N-phenylcarbamoyl)]saccharin in 125ml of dimethylformamide at 35° C is added all at once 4.9g (0.09 mole) of sodium methoxide. A considerable amount of heat is evolved and the mixture turns purple in color. Stirring is continued for one hour and it is poured into ice-water containing excess hydrochloric acid to cause precipitation of 5.5g of a tan solid, mp. 138°-144° C. This is dissolved in dichloromethane and extracted with aqueous sodium carbonate solution. Neutralization of the alkaline layer gives a precipitate which is collected and recrystallized from methanol to give 4.0g of product, mp. 148°-152° C dec.

Anal. Calcd. for C₁₆H₁₄N₂O₄S: C, 58.17; H, 4.27; N, 8.49; S, 9.71. Found: C, 58.33; H, 4.35; N, 8.42; S, 9.62.

EXAMPLE 5

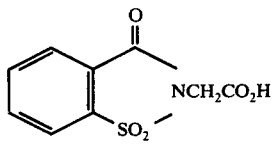

2-Carboxymethylsaccharin

The preparation of this substance has been described by Magidson et al., Ber., 56, 1810 (1928). The following is an alternate method which gives a purer product in higher yield.

A solution of 22.6g (0.11 mole) of sodium saccharin and 15g (0.1 mole) of tert-butyl α-chloroacetate in 150 ml of dimethylformamide is heated on a steam bath for 1 hour, allowed to stir at room temperature for 16 hours and poured into ice-water. The solution is dried over magnesium sulfate and the solvent is evaporated to give 24.9g of tert-butyl N-saccharinylacetate, m.p. 130°-132.5° C. This is refluxed with 300 ml of benzene and 1.4g (0.01 mole) of p-toluenesulfonic acid monohydrate to cause quantitative precipitation of 2-carboxymethylsaccharin, m.p. 212°-215° C. The completion of the reaction is established by passing a slow stream of nitrogen through the reaction mixture and into solution of bromine in carbon tetrachloride. Failure to decolorize the bromine indicates that no more isobutylene is being evolved.

EXAMPLE 6

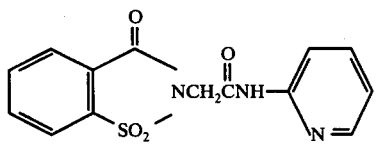

2-[(N-2-pyridylcarbamoyl)methyl]saccharin

Method A

A mixture of 2.4g (0.01 mole) of 2-carboxymethylsaccharin and 2.3g (0.011 mole) of dicyclohexyl carbodiimide in 50ml of tetrahydrofuran is stirred for 30 minutes and a solution of 0.94g of 2-aminopyridine in 25ml of tetrahydrofuran is added. The mixture is stirred at room temperature for three days and filtered. The filtrate is evaporated, the residue is triturated with a small amount of cold methanol and then recrystallized from methanol to give 1.6g of product, mp. 168°-171° C which is sufficiently pure for use as a starting material for further syntheses. Further recrystallization gives an analytical sample, mp. 174°-177° C.

Anal. Calcd. for C₁₄H₁₁N₃O₄S: C, 52.99; H, 3.49; N, 13.24; S, 10.10. Found: C, 52.97; H, 3.59; N, 13.28; S, 10.09.

Method B

A solution of 30g (0.125 mole) of 2-carboxymethylsaccharin, 11.75g (0.125 mole) of 2-aminopyridine, and 27.2g (0.138 mole) of N-ethoxycarbonyl-2-ethoxy-1,2-dihydroquinoline (EEDQ) in 500 ml of tetrahydrofuran is refluxed for 1 hour and then stirred at room temperature for 16 hours. Most of the tetrahydrofuran is removed by distillation in vacuo and the residue is partioned between water and chloroform. The chloroform layer is washed with 1N hydrochloric acid whereupon some solid precipitates. This is combined with the residue obtained on evaporation of the chloroform to give 27g of product, m.p. 168°-171° C which is of sufficient purity to be used in the subsequent reaction.

EXAMPLE 7

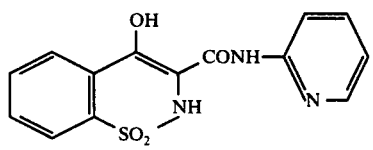

4-hydroxy-N-(2-pyridyl)-2H-1,2-benzothiazine-3-carboxamide 1,1-dioxide

Method A

To a solution of 3.2g (0.01 mole) of 2-[(N-2-pyridylcarbamoyl)methyl] saccharin in 10ml of warm dimethylsulfoxide is added 1.6g (0.03 mole) of sodium methoxide. The resulting slurry is heated quickly to 80°-90° C and then allowed to stand without external heating for 15 minutes. It is poured into ice-water, excess acetic acid is added, and it is filtered to give 1.4g of yellow product, mp. 223°-224° C dec. Recrystallization from acetic acid gives an analytical sample, mp. 223°-225° C dec.

Anal. Calcd. for C₁₄H₁₁N₃O₄S: C, 52.99; H, 3.49; N, 13.24; S, 10.10. Found: C, 52.79; H, 3.51; N, 13.18; S, 9.97.

Method B

To a solution of 9.6g (0.03 mole) of 2-[(N-2-pyridinylcarbamoyl)methyl]saccharin in 60 ml of dry dimethylformamide is added 4.9g (0.09 mole) of sodium methoxide. The temperature rises rapidly to 42° C and the color of the reaction mixture darkens to reddish purple. The temperature is then raised rapidly to 90° C, the heat source is removed and the mixture is allowed to stir for 50 minutes. It is then poured into 300 ml of ice-water to which 7 ml of acetic acid was previously added. The resulting yellow precipitates weighs 4.3g (45%) and has m.p. 221°-225° C dec. Recrystallization from acetic acid gives an analytical sample, m.p. 223°-225° C dec.

Found: C, 52.79; H, 3.51; N, 13.18; S, 9.95.

EXAMPLE 8

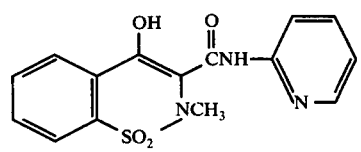

4-Hydroxy-2-methyl-N-(2-pyridyl)-2H-1,2-benzothiazine-3-carboxamide 1,1-Dioxide

To a slurry of 0.0037 mole of sodium hydride in 50 ml of dimethylformamide is added 1.1g (0.0034 mole) of 4-hydroxy-N-(2-pyridyl)-2H-1,2-benzothiazine-3-carboxamide 1,1-dioxide. When evolution of hydrogen ceases 0.4 ml of methyl iodide is added and the mixture is stirred at room temperature for 4 hours. It is poured into ice-water and the precipitate (0.5g) is collected. Recrystallization from methanol gives 0.4g of product, m.p. 195°–198° C dec. identical to a sample prepared by the method of Lombardino, *J. Med. Chem.*, 15, 848 (1972).

Anal. Calcd. for $C_{15}H_{13}N_3O_4S$: C, 54.37; H, 3.96; N, 12.68; S, 9.68. Found: C, 54.50; H, 4.20; N, 12.65; S, 9.62.

We claim:

1. 4-hydroxy-N-(2-pyridyl)-2H-1,2-benzothiazine-3-carboxamide 1,1-dioxide.